United States Patent [19]

Saeva et al.

[11] Patent Number: 4,738,964
[45] Date of Patent: Apr. 19, 1988

[54] METHOD OF SUPPRESSING THE IMMUNE SYSTEM COMPRISING ADMINISTERING 5H-THIAZOLO[2,3-B]QUINAZOLINE-3(2H)-ONE

[75] Inventors: Grace A. Saeva; Vassil S. Georgiev, both of Rochester, N.Y.

[73] Assignee: Pennwalt Corporation, Philadelphia, Pa.

[21] Appl. No.: 882,025

[22] Filed: Jul. 3, 1986

Related U.S. Application Data

[63] Continuation-in-part of Ser. No. 615,202, May 30, 1984, abandoned.

[51] Int. Cl.$^4$ ................ A61K 31/505; C07D 513/04
[52] U.S. Cl. .................................... 514/267; 544/250
[58] Field of Search ...................... 544/250; 514/267

[56] References Cited

U.S. PATENT DOCUMENTS

| | | | |
|---|---|---|---|
| 2,527,266 | 10/1950 | Kendall et al. | 544/250 |
| 4,083,980 | 4/1978 | Schromm et al. | 424/251 |
| 4,282,360 | 8/1981 | LeMahieu | 544/250 |
| 4,486,221 | 12/1984 | Seybold et al. | 544/250 X |
| 4,588,812 | 5/1986 | Saeva et al. | 544/250 |

FOREIGN PATENT DOCUMENTS 0098499 1/1984 European Pat. Off.

OTHER PUBLICATIONS

Lui et al., Arch Pharm., 316, pp. 569–571 (06/83).
Lui et al., Chemical Abstracts, vol. 99, 88155g (1983) (abstract of Lui et al., Arch. Pharm. 316, No. 6, pp. 569–571).
Grosso et al., J. Med. Chem., vol. 23, No. 11, pp. 1261–1264 (1980).

*Primary Examiner*—Donald G. Daus
*Assistant Examiner*—Diana G. Rivers

[57] ABSTRACT

The novel compound, 5H-thiazolo[2,3-b]quinazolin-3(2H)-one, and derivatives thereof in which a nuclear hydrogen of its benzene ring is replaced by lower alkyl, alkoxy, halogen, trifluoromethyl, $NO_2$ or $NH_2$; useful as anti-hypertensive agents and immunosuppressive agents.

1 Claim, No Drawings

METHOD OF SUPPRESSING THE IMMUNE SYSTEM COMPRISING ADMINISTERING 5H-THIAZOLO[2,3-B]QUINAZOLINE-3(2H)-ONE

This application is a continuation in part of application Ser. No. 615,202, filed May 30, 1984, now abandoned.

BACKGROUND OF THE INVENTION (1) Field of the Invention

This invention pertains to 5H-thiazolo[2,3-b]quinazolin-3(2H)-one and certain derivatives thereof.

(2) Description of the Prior Art

The synthesis of 5H-thiazolo-[2,3-b]quinazolin-3(2H)-one, and its anti-hypertensive activity, has been reported by Kang-Chien Liu et al, Arch. Pharm. (Weinheim) 316, 569–571 (1983, June issue). The synthesis of 2-(alkylamino)-3,4-dihydroquinazolines, and the extent to which they have anti-hypertensive activity, has been reported by J. A. Grosso et al, *J. Med. Chem.*, 23, 1261–1264 (1980).

BRIEF SUMMARY OF THE INVENTION

This invention relates to compounds of the formula

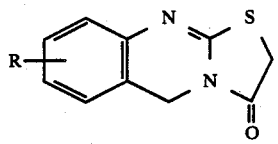

wherein R is H, lower ($C_1$–$C_4$) alkyl, alkoxy ($C_1$–$C_{18}$, branched or unbranched chain), halogen, trifluoromethyl, $NO_2$ or $NH_2$.

DETAILED DESCRIPTION

Utility

The compounds of this invention are useful as anti-hypertensive agents and immunosuppressive agents. The compound, 5H-thiazolo[2,3-b]quinazolin-3(2H)-one has been shown to have anti-hypertensive activity by Kang-Chien Liu et al, Arch. Pharm. (Weinheim) 316, 569–571 (1983, June issue).

Compounds

The compounds of this invention are those of the formula

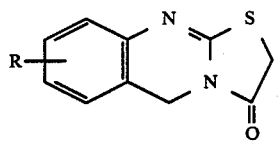

wherein R is H, lower ($C_1$–$C_4$) alkyl, alkoxy ($C_1$–$C_{18}$, branched or unbranched chain), halogen, trifluoromethyl, $NO_2$ or $NH_2$.

Formation of the Compounds (1) Preparation of 3,4-dihydro-2(1H)-quinazolinethione optionally substituted in its benzene ring The reaction is summarized as follows:

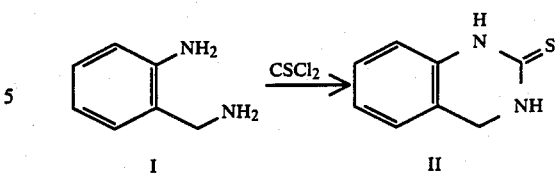

This reaction is performed as described by Grosso et al, *J. Medicinal Chem.*, vol. 23, p. 1261–1264 (1980). Replacement of 2-aminobenzylamine (compound I) by a derivative thereof in which a nuclear hydrogen of the benzene ring is substituted with lower alkyl, alkoxy, halogen, trifluoromethyl, $NO_2$ or $NH_2$, results in the corresponding derivative of 3,4-dihydro-2(1H)-quinazolinethione (compound II).

(2) Preparation of 5H-thiazolo[2,3-b]quinazolin-3(2H)-one optionally substituted in its benzene ring The preparation of 5H-thiazolo[2,3-b]quinazolin-3(2H)-one is summarized as follows:

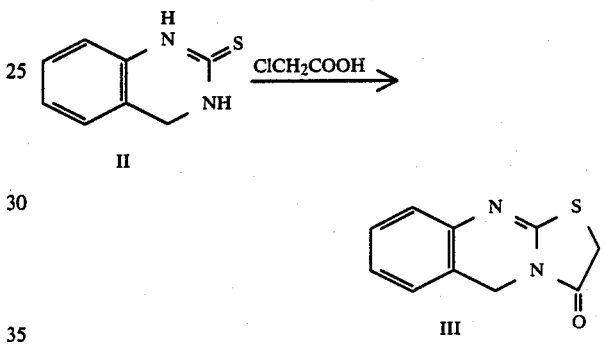

A mixture of 1.0 g (0.006 mol) 3,4-dihydro-2(1H)-quinazolinethione (compound II), 0.57 g (0.006 mol) chloroacetic acid, and 0.54 g (0.0065 mol) sodium bicarbonate is mixed in 31.25 ml water, and heated overnight at 90° C. Then, 12.5 ml of dimethylformamide is added, and the reaction mixture is refluxed for 6½ hours. After cooling, 5H-thiazolo[2,3-b]quinazolin-3(2H)-one, as the precipitated solid, is filtered off and recrystallized from anhydrous ethanol. Replacement of 3,4-dihydro-2(1H)-quinazolinethione by a derivative thereof in which a nuclear hydrogen of the benzene ring has been substituted with lower alkyl, alkoxy, halogen, trifluoromethyl, $NO_2$ or $NH_2$, results in the corresponding derivative of 5H-thiazolo[2,3-b]quinazolin-3(2H)-one.

ILLUSTRATIVE EXAMPLE

A mixture of 1.0 g (0.006 mol) 3,4-dihydro-2(1H)-quinazolinethione, 0.57 g (0.0065 mol) chloroacetic acid, and 0.54 g (0.0065 mol) sodium bicarbonate were mixed in 31.25 ml water, and heated overnight at 90° C. Then, 12.5 ml of dimethylformamide were added, and the reaction mixture was refluxed for 6½ hours. After cooling, the precipitated solid was filtered off and recrystallized from anhydrous ethanol. Yield—0.50 g. Mp 203°–205° C.

Anal. Calcd for $C_{10}H_8N_2SO$: C, 58.81; H, 3.95; N, 13.72; S, 15.70. Found: C, 59.03; H, 4.12; N, 13.70; S, 15.79.

Immunosuppressive activity can be shown in the Kennedy Plaque Assay, a method devised by N. K. Jerne et al, "The Agar Technique for Recognizing Antibody Producing Cells" in *Cell Bound Antibodies* (B.

Amos and H. Koprowski, Eds.) Wistar Press, Philadelphia, PA, pp. 109–125 (1963) and modified by J. C. Kennedy and M. A. Axelrod, Immunology 20, 253 (1971), as follows:

Female mice of strain C3H at a body weight of 18–23 g are housed for 5 days, and allowed food and water ad libitum prior to intraperitoneal (ip) administration of 0.2 ml of a 20% suspension of T-dependent antigen sheep erythrocytes (SRBC). The test compound is administered ip on three successive days, the first administration occurring 24 hr. following the administration of the SRBC. Twenty-four hours after the final administration of the test compound, the mice are killed, their spleens aseptically removed and spleen cells ("test cells") suspended in Dulbecco's PBS medium.

A two ml suspension of test cells at a concentration of $5 \times 10^4$/ml, mixed with 0.2 ml of guinea pig complement that has been absorbed with packed SRBC, is added to a monolayer of SRBC adsorbed to the bottom of a $60 \times 15$ mm plastic tissue culture petri dish. [The SRBC are adsorbed to a dish by a four step process: (1) the dish is incubated with poly-L-lysine (0.025 mg/ml in PBS) for 15 min; (2) the poly-L-lysine is decanted and the dish rinsed with PBS to eliminate the excess poly-L-lysine; (3) two ml of a 1% solution of SRBC in PBS is then added to each dish for 15 min at room temperature (about 25° C.), gently agitated, and then incubated for another 15 min; (4) the SRBC suspension is poured off, and then rinsed off with PBS.]

After the test cells and complement have been incubated with the monolayer of SRBC for 1 hr 30 mins., in a humidified $CO_2$ incubator at 37° C., they are drained off and the monolayer cells fixed with a 1% solution of glutaraldehyde. Medium and large plaques are counted.

The above procedure was used to test 5H-thiazolo[2,3-b]quinazolin-3(2H)-one administered at a concentration of 1.56 mg/kg/day on three successive days, 6.25 mg/kg/day on three successive days, and 25 mg/kg/day on three successive days. [Each dosage is based on the weight of the hydrochloride salt of the test compound] For each concentration of test compound, 3 groups of 4 mice were tested. The control value (plaques obtained when spleen cells from mice unexposed to the test compound were added to the culture dishes) was 75.9 plaques/$10^5$ spleen cells. When doses of 1.56, 6.25 and 25 mg/kg/day, respectively, were tested, the number of plaques were 76%, 72% and 81%, respectively, of the control value. The results obtained with 6.25 mg/kg indicated statistically significant ($P<0.05$) immunosuppression. The results obtained with 1.56 and 25 mg/kg indicated a tendency to achieve immunosuppression, but the results were not significant at the $P<0.05$ level.

The compounds of this invention can be administered in other mammals, including humans to achieve immunosuppression. In addition to the ip route, the iv, sc and po routes are possible. Although one has the option of using the test data with mice as a starting point for use of a compound in humans, the more prudent course would be to titrate a given compound in humans in order to determine the optimum dose.

What is claimed is:

1. A method of suppressing the immune system comprising the administration, to a mammal in need of such treatment, of an effective amount of a compound of the formula

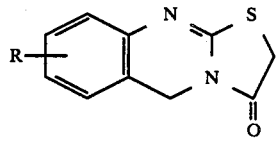

wherein R is H.

* * * * *